(12) United States Patent
Dolbier et al.

(10) Patent No.: US 7,230,115 B1
(45) Date of Patent: Jun. 12, 2007

(54) PREPARATION OF COMPOUNDS USEFUL FOR THE DETECTION OF HYPOXIA

(75) Inventors: William R Dolbier, Gainesville, FL (US); An-Rong Li, South San Francisco, CA (US); Cameron J Koch, Aldan, PA (US); Alexander V Kachur, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/297,454

(22) PCT Filed: Apr. 20, 2000

(86) PCT No.: PCT/US00/40437

§ 371 (c)(1),
(2), (4) Date: May 15, 2003

(87) PCT Pub. No.: WO01/07414

PCT Pub. Date: Feb. 1, 2001

Related U.S. Application Data

(60) Provisional application No. 60/144,747, filed on Jul. 21, 1999.

(51) Int. Cl.
 *C07D 233/91* (2006.01)
(52) U.S. Cl. ............... 548/327.5; 548/338.1
(58) Field of Classification Search ............. 548/327.5, 548/338.1
 See application file for complete search history.

(56) References Cited

U.S. PATENT DOCUMENTS

| | | | |
|---|---|---|---|
| 3,505,349 A | 4/1970 | Beaman et al. | 260/309 |
| 5,540,908 A * | 7/1996 | Koch et al. | 424/9.34 |
| 5,721,265 A | 2/1998 | Tracy et al. | 514/396 |
| 5,843,404 A | 12/1998 | Koch et al. | 424/934 |
| 6,252,087 B1 | 6/2001 | Koch et al. | 548/327.5 |

OTHER PUBLICATIONS

Adams, G.E., "Hypoxia-mediaed drugs for radiation and chemotherapy," *Cancer*, 1981, 48(3), 696-707.
Castelhano, A.L., et al., "Reactions of an electrophilic glycine cation equivalent with grignard reagents a simple synthesis of β,δ—unsaturated amino acids," *Tetrahedron Letts.*, 1986, 27(22), 2435-2438.
Castelhano, A.L., et al., "Synthesis of α-amino acids with β, γ-unsaturated side chains," *Tetrahedron Letters*, 1988, 44(17), 5451-5466.
Chapman, J.D., et al., "The fraction of hypoxic clonogenic cells in tumor populations," in *Biological Bases and Clinical Implications of Tumor Radioresistance*, 1983, Fletcher, G.H., et al. (Eds.), 61-73.

Chapman, J.D., et al., "Keynote address: Cellular reduction of nitroimidazole drugs: potential for selective chemotherapy and diagnosis of hypoxic cells," *Int. J. Radiat. Oncol. Biol. Phys.*, 1989, 16, 911-917.
Evans, S.M., et al., "Noninvasive detection of tumor hypoxia using the 2-nitroimidazole [$^{18}$F]EF1," *J. of Nuclear Medicine*, 2000, 41, 327-336.
Franko, A.J., et al., "Oxygen dependence of binding of misonidazole to rodent and human tumors *in vitro*," *Cancer Res.*, Oct. 15, 1987, 47, 5367-5376.
Grierson, J.R., et al., "A radiosynthesis of fluorine-18 fluoromisonidazole," *J. of Nuclear Medicine*, Mar. 1989, 30(3), 343-350.
Jerabek, P.A., et al., "Synthesis and biodistribution of $^{18}$F-labeled fluoronitroimidazoles: potential *in vivo* markers of hypoxic tissue," *Applied Radiation & Isotopes*, 1986, 37(7), 599-605.
Kachur, A.V., et al., "Synthesis of new hypoxia markers EF1 and [$^{18}$F]-EF1," *J. of Applied Radiation and Isotopes*, 1999, 51(6), 643-650.
Kennedy, K.A., et al., "Commentary: The hypoxic tumor cell: a target for selective cancer chemotherapy," *Biochem. Pharm.*, 1980, 29, 1-8.
Koch, C.J., et al., "Metabolism induced binding of $^{14}$C-misonidazole to hypoxic cells: kinetic dependence on oxygen concentration and misonidazole concentration," *Int. J. Radiation Oncology Biol. Phys.*, 1984, 10, 1327-1331.
Koch, C.J., "The reduction activation of nitroimidazoles; modification by oxygen and other redox-active molecules in cellular systems," *Selective Activation of Drugs by Redox Processes*, Adams, G.E., et al (Eds.), 1990, 237-247.
Koch, C.J., "The mechanisms of radiation protection by non-protein sulfhydryls: glutathione, cysteine, and cysteamine," *CRC Press*, 1998, 25-52.
Koh, W.-J., et al., "Postron emission tomography," *Acta Oncologica*, 1994, 33(3), 323-327.
Koh, W.-J., et al., "Imaging of hypoxia in human tumors with [F-18]fluoromisonidazole," *International J. of Radiation Oncology, Biology Physics*, 1991, 22, 199-212.
Mathias, C.J., et al., "Radiolabelled hypoxic cell sensitizers: tracers for assessment of ischemia," *Life Sciences*, 1987, 41, 199-206.
Moulder, J.E., et al., "Hypoxic fractions of solid tumors: experimental techniques, methods of analysis, and a survey of existing data," *Int. J. Radioat. Oncol. Biol. Phys.*, 1984, 10, 695-712.
Ohah, G.A., et al., "Synthetic methods and reactions II. Halofluorination of alkenes in poly-hydrogen fluoride/pyridine solution," *Synthesis*, Dec. 1973, 4, 780-783.
Pariament, M.B., et al., "None-invasive assessment of human tumour hypoxia with $^{123}$I-idoazomycin arabinoside: preliminary report of clinical study," *Br. J. Cancer*, 1992, 65, 90-95.

(Continued)

*Primary Examiner*—Kamal A. Saeed
(74) *Attorney, Agent, or Firm*—Woodcock Washburn, LLP

(57) ABSTRACT

Novel $^{18}$F-flourine compounds useful for non-invasive imaging techniques such as PET, for detecting tissue hypoxia, and methods for preparing them are disclosed. Novel intermediate compounds and methods for preparing them are also disclosed. Diagnostic kits useful in practicing the methods of claimed invention are also provided.

14 Claims, 3 Drawing Sheets

OTHER PUBLICATIONS

Raleigh, J.A., et al., "Fluorescence immunohistochemical detection of hypoxic cells in spheroids and tumours," *Br. J. Cancer*, 1987, 56, 395-400.

Raleigh, J.A., et al., "Reductive fragmentation of 2-nitroimidazoles: amines and aldehydes," *Int. J. Radiat. Oncol. Biol. Phys.*, 1984, 10, 1337-1340.

Rasey, J.S., et al., "Characterization of [$^{18}$F]fluoroetanidazole, a new radiopharmaceutical for detecting tumor hypoxia," *J. of Nuclear Medicine*, Jun. 1999, 40(6), 1072-1079.

Rasey, J.S., et al., "Characterization of radiolabeled fluoromisonidazole as a probe for hypoxic cells," *Radiation Res.*, 1987, 111, 292-304.

Taylor, Y.C., et al., "Differences in toxicity and metabolism of the 2-nitromidazole misonidazole (Ro-07-0582) in hela and Chinese hamster ovary cells," *Cancer Res.*, 1978, 38, 2745-2752.

Tewson, T.J., "Synthesis of [$^{18}$F]fluoroetanidazole: a potential new tracer for imaging hypoxia," *Nuclear Medicine & Biology*, 1997, 24, 755-760.

Valk, P.E., "Hypoxia in human gliomas: demonstration by PET with fluorine-18-fluoromisonidazole," *J. Nucl. Med.*, 1992, 33, 2133-2137.

Varghese, A.J., et al., "Binding to cellular macromolecules as a possible mechanism for the cytotoxicity of misonidazole," *Cancer Res.*, Jul. 1980, 40, 2165-2169.

Williams, R.M., et al., "General synthesis of β,γ-alkynylglycine derivatives," *J. Org. Chem.*, 1990, 55, 4657-4663.

Yang, D.J., et al., "Development of F-18-labeled fluoroerythronitroimidazole as a PET agent for imaging tumor hypoxia," *Radiology*, Mar. 1995, 194, 795-800.

Yeh, S.-H., et al., "fluorine-18 fluoromisonidazole tumour to muscle retention ration for the detection of hypoxia in nasopharyngeal carcinoma," *Europ. J. of Nuclear Medicine*, Oct. 1996, 23(10), 1378-1383.

Copy of the Supplementary European Search Report dated Jun. 24, 2004 (EP 00 96 0168).

Walch, N.S., et al., "Mapping of the vascular endothelial growth factor-producing hypoxic cells in multicellular tumor spheroids using a hypoxia-specific marker," *Cancer Research*, 1995, 55, 6222-6226.

Ido, T. et al., "Fluorination with F2-A Convenient Synthesis of 2-Deoxy-2-Fluoro-D-Glucose", *J. Org. Chem.*, 1977, 42(13), 2341-2342.

\* cited by examiner

PREPARATION OF COMPOUNDS USEFUL FOR THE DETECTION OF HYPOXIA

CROSS-REFERENCE TO RELATED APPLICATIONS

This application is the United States national phase of International Application No. PCT/US00/40437, filed Jul. 20, 2000, which claims benefit under 35 U.S.C. §119(e) of U.S. Provisional Application No. 60/144,747, filed Jul. 21, 1999, which is incorporated by reference herein in their its entirety entireties.

FIELD OF THE INVENTION

This invention generally relates to novel fluorine compounds and methods for preparing them that enable labeling by radioactive isotope $^{18}F$. These compounds allow the imaging of tissues using imaging techniques such as positron emission tomography (PET). For example, a group of nitroaromatic compounds has been prepared which when activated by reductive metabolism, bind to hypoxic cells. This reductive metabolism and binding increase as the oxygen concentration of the cells decreases, thus making these compounds good indicators of tissue hypoxia. Using the compounds and methods of the invention, tissue hypoxia may be detected using non-invasive methods, such as imaging techniques involving specific radioactive isotopes attached to the drug.

BACKGROUND OF THE INVENTION

One of the most important goals in oncology is the identification and elimination of treatment resistant cells; hypoxic cells are the most familiar examples of this type of cell. See, Kennedy, et al., *Biochem. Pharm.* 1980, 29, 1; Moulder, et al., *Int. J. Radioat. Oncol. Biol. Phys.* 1984, 10, 695; Adams, *Cancer*, 1981, 48, 696, all of which are incorporated herein by reference in their entirety. Hypoxic cells are seldom found in normal tissues, and are generally found only in conjunction with certain tumors, vascular diseases, wounded tissue, or after a stroke.

As certain tumors enlarge, the tissue often outgrows its oxygen and nutrient supply because of an inadequate network of functioning blood vessels and capillaries. Although the cells deprived of oxygen and nutrients may ultimately die, at any given time a tumor may produce viable hypoxic cells. These hypoxic cells, although alive, have very low oxygen concentrations because of their remoteness from the blood vessels.

The level of molecular oxygen has important implications in disease diagnosis and prognosis. In medical oncology, for example, hypoxic cells in solid tumors may be highly resistant to killing by some forms of chemotherapy. When chemotherapeutic agents are administered to patients, the agents are carried through the functioning blood vessels and capillaries to the target tissue. Because hypoxic tissue lacks a fully functioning blood supply network, the chemotherapeutic drugs may never reach the hypoxic cells; instead, intervening cells scavenge the drug. The result is that the hypoxic cells survive and recurrence of the tumor is possible. Kennedy, et al., supra.

Tissue hypoxia also hinders the effectiveness of radiation therapy against tumors. Radiation treatment is most effective in destroying oxygen containing cells because oxygen is an excellent radiation sensitizer. The presence of hypoxic cells impedes this treatment because their low oxygen concentration renders the ionizing radiation relatively ineffective in killing the cancerous cells. Therefore, hypoxic cells are more likely to survive radiation therapy and eventually lead to the reappearance of the tumor. The importance of hypoxic cells in limiting radiation responsiveness in animal tumors is well known, Adams, supra; Moulder, et al., supra; Chapman, et al., "The Fraction of Hypoxic Clonogenic Cells in Tumor Populations," in *Biological Bases and Clinical Implications of Tumor Radioresistance* 61, G. H. Fletcher, C. Nevil, & H. R. Withers, eds., 1983. Studies have revealed that such resistant cells greatly affect the ability of radiation and chemotherapy to successfully sterilize tumors in animals. Substantial work since that time has shown similar problems in human tumors. Despite the progress in animal studies regarding the identification of hypoxic cells, limited success has been achieved in humans. One reason for this disparity may relate to differences in tumor growth and other host related factors, but in addition, there has been no suitably accurate method to assess tissue oxygen at a sufficiently fine resolution.

Venous oxygen pressure is generally ~35 Torr, an oxygen level providing nearly full radiation sensitivity. As the oxygen level decreases below 35 Torr, radiation resistance gradually increases, with half-maximal resistance at about 3.5 Torr, and full resistance at about 0.35 Torr. Therefore, it is necessary to measure much lower oxygen levels than are usually encountered in normal tissue. Current technology does not meet this need.

Nitroheterocyclic drugs have been under extensive investigation as hypoxia markers. It is known that this class of compounds can provide sufficient sensitivity to monitor the low oxygen partial pressures described above. This technique involves the administration of nitroaromatic drugs to the tissue of interest. The drugs undergo bioreductive metabolism at a rate which increases substantially as the tissue's oxygen partial pressure decreases. The result of this bioreductive metabolism is that reactive drug products are formed which combine chemically to form adducts with predominantly cellular proteins. Because the metabolic binding of these compounds to cellular macromolecules is inhibited by oxygen, these compounds bind to hypoxic cells in preference to normal, healthy, oxygen-rich tissue. This preferential metabolic binding, or adduct formation, provides a measure of the degree of hypoxia. Koch, et al., *Int. J. Radiation Oncology Biol. Phys.*, 1984,10, 1327.

Misonidazole (MISO) 3-methoxy-1-(2-nitroimidazol-1-yl)-2-propanol and certain of its derivatives have been under extensive investigation as indicators of hypoxia in mammalian tissue. Chapman, et al., *Int. J. Radiat. Oncol. Biol. Phys.*, 1989,16, 911; Taylor, et al., *Cancer Res.*, 1978, 38, 2745; Varghese, et al., *Cancer Res.*, 1980, 40, 2165. The ability of certain misonidazole derivatives to form adducts with cellular macromolecules, referred to as binding throughout this application, has formed the basis of various detection methods.

For example, $^3H$ or $^{14}C$ labeled misonidazole has been used in vitro and in vivo, with binding analyzed by liquid scintillation counting or autoradiography. Chapman, 1984 supra; Urtasun, 1986, supra; Franko, et al., *Cancer Res.*, 1987, 47, 5367. A monofluorinated derivative of misonidazole has utilized the positron emitting isotope $^{18}F$ for imaging bound drug in vivo, Rasey, et al., *Radiat. Res.*, 1987, 111,292. The method of the preparation of the PET derivative of ethanidazole was described in Tewson T. J., *Nuclear Medicine & Biology*, 1997 24(8):755–60. An iodine isotope has been incorporated into another azomycin derivative, azomycin arabinoside, allowing radiology techniques of detection. Parliament, et al., Br. *J. Cancer,* 1992, 65, 90.

A hexafluorinated derivative of misonidazole 1-(2-hydroxy-3-hexafluoro-isopropoxy-propyl)-2-nitroimidazole has been assayed directly (no radioactive isotopes) via nuclear magnetic resonance spectroscopy (NMR or MRI) techniques. Raleigh, et al., *Int. J. Radiat. Oncol. Biol. Phys.,* 1984, 10, 1337. Polyclonal antibodies to this same derivative have allowed immunohistochemical identification of drug adducts. Raleigh, et al., Br. *J. Cancer,* 1987, 56, 395.

The bioreductive drug assays described above do not directly measure oxygen partial pressure, even though this is the required value, using the example of radiation therapy to predict radiation response. Rather, the assays measure adduct formation, a biochemical process which is inhibited by oxygen. The data generated using these methods has shown that the degree of inhibition by oxygen varies substantially from tissue to tissue. Franko, et al., 1987, supra. Furthermore, the maximum rate of adduct formation in the complete absence of oxygen is also highly variable from tissue to tissue, as is the maximum percentage of inhibition by oxygen, Koch, in *Selective Activation of Drugs by Redox Processes,* Plenum Press, pp. 237–247, Adams, et al., eds, New York, 1990. Another way of expressing these limitations is that the bioreductive formation of nitroaromatics provides only a relative indication of varying oxygen levels, but is inadequate at providing an absolute measurement of oxygen partial pressure because there are several factors which affect adduct formation in addition to changes in oxygen, non-oxygen-dependent factors. Additionally, the choice of nitroaromatic drug affects the variability related to the non-oxygen-dependent factors.

Early research efforts (i.e., before the invention claimed in U.S. Pat. No. 5,540,908 on Nov. 19, 1992) had focused on misonidazole and certain of its derivatives. However, misonidazole is the most susceptible of several drugs tested to non-oxygen-dependent variations in adduct formation. Koch, Selective Activation, supra. Other problems relate to various physicochemical properties of existing drugs, all of which can influence the non-oxygen dependent variations in adduct formation. For example, the hexafluorinated misonidazole derivative described above had a high degree of insolubility.

Thus, we have focused our previous study on a 2-nitroimidazole which has greatly superior properties to misonidazole for the purpose of hypoxia detection This drug is 2-(2-nitro-1H-imidazol-1-yl)-N-(2,2,3,3,3-pentafluoropropyl) acetamide (hereinafter referred to as EF5), and 2-(2-nitro-1H-imidazol-1-yl)-N-(3,3,3-trifluoropropyl) acetamide (hereinafter referred to as EF3), see, U.S. Pat. No. 5,540,908, issued to Koch et al., the disclosure of which is herein incorporated by reference in its entirety, as well as (N-(3-fluoropropyl)-2-(2-nitroimidazol-1[H]-yl)-acetamide (EF1), see U.S. Ser. No. 09/123,300, also incorporated herein by reference and assigned to the same entity. Our previous studies have employed monoclonal antibodies to detect the adducts of EF3 and EF5.

Incorporation of $^{18}$F into 2-nitroimidazole compounds provides an opportunity to use these agents for the detection of hypoxia by positron emission tomography (PET). See, Jerabek, et al., *Applied Radiation & Isotopes,* 1986 37 (7), 599–605; see, Mathias et al., "Radiolabelled hypoxic cell sensitizers: tracers for assessment of ischemia," *Life Sciences,* 1987 41 (2), 199–206. Several groups have developed $^{18}$F-labeled nitroimidazole-based PET assays, for example, [$^{18}$F]-fluormisonidazole. See, Rasey et al, *Radiation Research,* 1987 111, (2),292–304; Rasey et al., *Int'l J. of Rad. One., Bio., Phys.,* 1996 36(2),417–428; Grierson, *Journal of Nuclear Medicine,* 1989 30 (3), 343–50; Koh, et al., *International Journal of Radiation Oncology, Biology, Physics,* 1992 22 (1), 199–212; [$^{18}$F]-fluoroerythronitroimidazole, See, Yang, et al., *Radiology,* 1995 194 (3), 795–800; and, [$^{18}$F]-fluoroetanidazole, See, Tewson, *Nuclear Medicine & Biology,* 1997 24 (8), 755–60.

The first described and most investigated compound of this type is [$^{18}$F]-fluoromisonidazole. This agent has been studied in several anatomic sites in humans including gliomas, see, Valk, et al. *Journal of Nuclear Medicine,* 1992 33 (12), 2133–7; lung cancer, see, Koh, et al., *Acta Oncologica,* 1994 33 (3),323–7; and nasopharyngeal carcinoma, see, Yeh, et al, *European Journal of Nuclear Medicine,* 1996 23 (10), 1378–83. However, despite the extensive investigations, none of these currently developed compounds is accepted clinically as a PET marker of hypoxia. For example, it has been shown that [$^{18}$F]-fluoromisonidazole is not stable in vivo, and produces multiple radioactive products distinct from the parent drug following renal clearance. See, Rasey, et al., *Journal of Nuclear Medicine,* 1999 40 (6), 1072–9. Our goal, therefore, has been to employ all the other beneficial aspects of hypoxia detection by EF5, including high drug stability in vivo, ability to cross blood-brain barrier, etc., with non-invasive detection of $^{18}$F incorporated into its molecular structure.

Recently, [$^{18}$F]-EF1 compounds have been developed as PET hypoxia markers. This compound was synthesized using nucleophilic substitution of the bromine atom of a precursor 2(2-nitroimidazol-1[H]-yl)-N-(3-bromopropyl)-acetamide by [$^{18}$F]-F-. See, Kachur et al., *Journal of Applied Radiation and Isotopes,* 1999, 51 (6), 643–650. [$^{18}$F]-EF1 has shown good potential for labeling of hypoxic tumors and a relatively uniform biodistribution limited by slow equilibration with brain tissue Evans, et al., *Journal of Nuclear Medicine,* 2000 Vol. 41, 327–336. As EF5 has been shown to predict radiotherapy resistance in individual rodent tumors with well documented pharmacological properties, attempts were made to label this compound with $^{18}$F for use in non-invasive imaging techniques. Until now, attempts to incorporate $^{18}$F into a site already containing other fluorine atoms have been unsuccessful. Thus, a need exists for new methods of incorporating $^{18}$F labels into compounds that are useful in non-invasive imaging techniques, such as PET.

SUMMARY OF THE INVENTION

This invention presents novel techniques for incorporating $^{18}$F labels into compounds that are useful for non-invasive assays such as PET imaging. The invention also includes novel compounds useful in such methods, as well as novel $^{18}$F-labeled compounds. The novel compounds of the invention and the methods according to this invention provide the basis for sensitive and precise methods for detecting tissue hypoxia.

According to one aspect of the present invention, methods are provided for the electrophilic fluorination of fluorinated alkenyl compounds comprising the step of contacting a fluorinated precursor having the formula I:

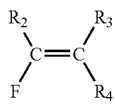

wherein $R_2$, $R_3$, and $R_4$ are independently selected from the group consisting of H, halogen, alkyl heteroalkyl, cycloalkyl heterocycloalkyl, aryl, heteroaryl, alkoxy, aminoalkyl, hydroxyalkyl ether, amide, keto, and carboxyl;

with $F_2$ in the presence of an organic solvent, such as trifluoroacetic acid, for a time and under conditions effective to form a compound having the formula II:

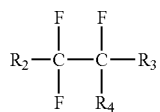

In further preferred embodiments, one of $R_2$, $R_3$, and $R_4$ is a nitroaromatic group, and the other of $R_2$, $R_3$, and $R_4$ are, independently, hydrogen or fluorine. A preferred nitroaromatic group of the present invention has the formula III:

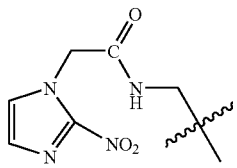

In certain embodiments, methods are provided for incorporating $^{18}F$ into compounds of formula II by contacting precursors of Formula I with [$^{18}F$]-$F_2$ in the presence of an organic solvent for a time and under conditions effective to produce the [$^{18}F$]-labeled compounds.

According to one aspect of the present invention, compounds are provided having formula IV:

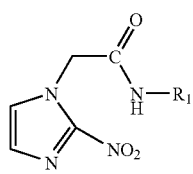

wherein $R_1$ is selected from the group consisting of —$CH_2$—CHF—$CH_2F$, —$CH_2CHFCHF_2$, —$CH_2$—$CF_2$—$CH_2F$, —$CH_2CHFCF_3$, —$CH_2CF_2CHF_2$, and —$CH_2CF_2CF_3$;

provided that at least one F is an $^{18}F$ isotope. In certain preferred embodiments, $R_1$ is —$CH_2CF_2CF_3$. These compounds may be referred to as EF1,1; EF1,2; EF2,1; EF1,3; EF2,2; and EF2,3 (or EF5) compounds, wherein the number designates the degree of fluorination on the last two carbon atoms on the side chain. Because EF2,3 has no isomers, it will be referred to by its previously accepted name EF5. For example, EF 1,1 has the side chain —$CH_2$—CHF—$CH_2F$, while EF5 has the side chain —$CH_2CF_2CF_3$.

Compounds of formula IV are prepared from allyl precursors having the following formula V according to the methods of the present invention:

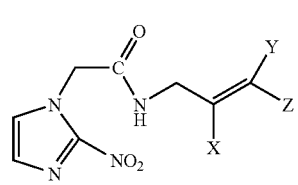

wherein X, Y, and Z are independently H or F, depending on the level of fluorination desired in the final product.

According to another aspect of the present invention, methods for detecting tissue hypoxia in a mammal are disclosed comprising the steps of:

(a) introducing into a mammal a compound having the formula IV:

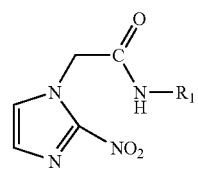

wherein $R_1$ is selected from the group consisting of —$CH_2CHFCH_2F$, —$CH_2CHFCHF_2$, —$CH_2CHFCF_3$, —$CH_2CF_2CHF_2$, and —$CH_2CF_2CF_3$ and at least one F is $^{18}F$; and (b) imaging a portion of the mammal containing the tissue with PET or SPECT imaging techniques.

Kits useful for diagnostic applications comprising the novel compounds or compositions are also within the ambit of the present invention. These kits include a drug formulation of a compound of the invention. The compounds of the invention are very useful in detecting oxygen levels because of their dramatic specificity for hypoxic cells over normal, healthy, oxygenated tissue.

DETAILED DESCRIPTION OF PREFERRED EMBODIMENTS

Figure 1:
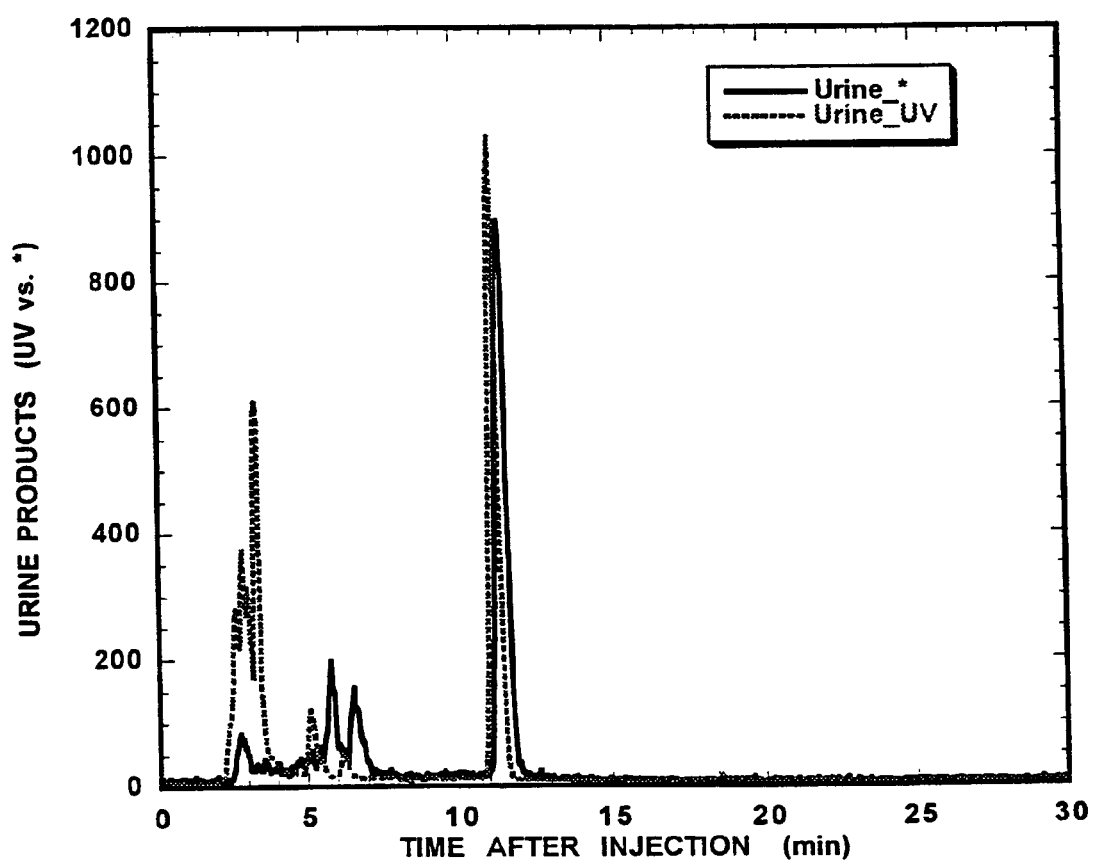
FIG. 1 represents an HPLC analysis of the reaction mixture of the product of [$^{18}F$]-EF5 synthesis.
Figure 2:
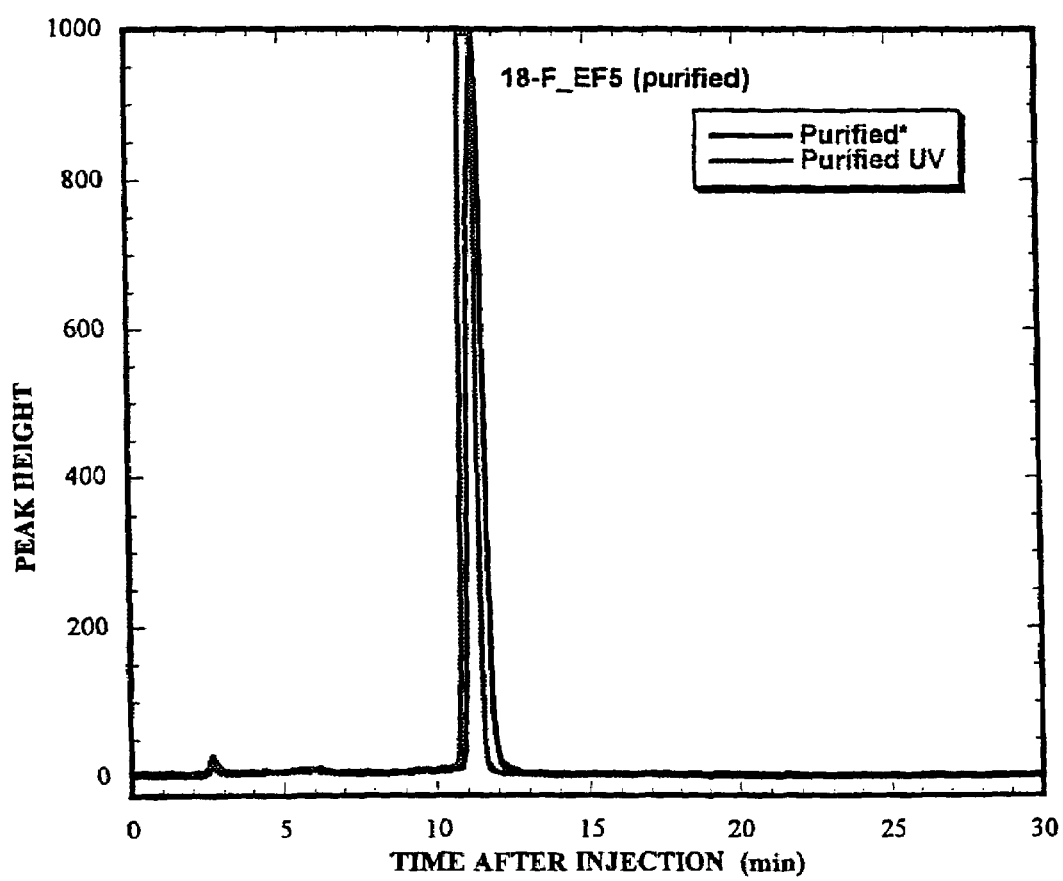
FIG. 2 represents an HPLC analysis of purified [$^{18}F$]-EF5; chemical and radiochemical purity of the sample >99%.

The present invention presents novel compounds that are useful oxygen predictors amenable to non-invasive assays, such as PET (positron emission tomography), methods for preparing them, and novel intermediates, referred to herein as allyl precursors. Specifically, the invention is directed to novel methods for fluorinating allyl precursors resulting in novel fluorine-18 ($^{18}$F) PET compounds. $^{18}$F exhibits excellent nuclear and chemical properties. These compounds are advantageous for metabolite, inter alia, and plasma analysis. Additionally, transport of $^{18}$F compounds to hospitals lacking an on-site cyclotron is easily accomplished due to the its half-life of $^{18}$F, which is approximately 110 minutes.

The novel compounds, compositions, and corresponding methods provide techniques for measuring the degree of hypoxia in mammalian tumors with good precision and sensitivity. These novel compounds and compositions may be used to detect hypoxia using standard nuclear medical procedures with great consistency. These novel compounds thus afford the opportunity to study and compare their biodistribution using macroscopic non-invasive (PET, SPECT) methods at drug concentrations appropriate for each method, but also to compare methods at constant drug concentration. This allows for much new information on the pharmacology and biodistribution of such molecules.

According to methods of the present invention, methods are disclosed for providing PET compounds comprising the step of contacting a fluorinated alkenyl precursor having the formula I:

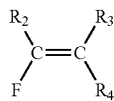

I wherein $R_2$, $R_3$, and $R_4$ are independently selected from the group consisting of H, halogen, alkyl heteroalkyl cycloalkyl heterocycloalkyl, aryl heteroaryl alkoxy, aminoalkyl hydroxyalkyl ether, amide, keto, and carboxyl;

with [$^{18}$F]-F$_2$ in the presence of an organic solvent, such as trifluoroacetic acid, for a time and under conditions effective to form a compound having the formula II:

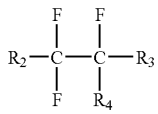

II wherein at least one of the F groups is $^{18}$F.

In instances where unlabeled polyfluorinated compounds are desired, compounds of formula I may be contacted with F$_2$, rather than [$^{18}$F]-F$_2$ to yield the unlabeled polyfluorinated compounds of formula II.

Alkyl groups suitable for the invention include substituted or unsubstituted straight or branched chain $C_1$-$C_{20}$ hydrocarbons. Suitable aryl groups include, but are not limited to, substituted or unsubstituted aryl groups such as, phenyl, condensed aromatic moieties, e.g., mono-, bi-, or tri-aryl and heterocyclic moieties. Heteroatoms of the invention include —N and —O. The term "substituted" includes single or multiple substitutions of a molecule with a moiety or moieties distinct from the core molecule. Substituents include, without limitation, halogens, hetero atoms, nitro moieties, amino moieties, heteroatom derivatives such as hydroxy moieties, alkoxy moieties, phenoxy moieties, amido, and other aliphatic or aromatic moieties.

In a preferred embodiment, PET compounds having formula IV:

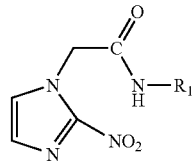

IV wherein $R_1$ is selected from the group consisting of —CH$_2$—CHF—CH$_2$F (EF1,1), —CH$_2$CHFCHF$_2$ (EF1,2), —CH$_2$—CF$_2$—CH$_2$F (EF2,1), —CH$_2$CHFCF$_3$ (EF1,3), —CH$_2$CF$_2$CHF$_2$ (EF2,2), and —CH$_2$CF$_2$CF$_3$ (EF5); and provided that at least one F is an $^{18}$F isotope; are prepared from allyl precursors having formula V:

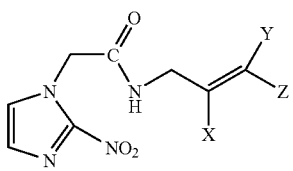

V wherein X, Y, and Z are independently H or F. The level of fluorination of the allylic sidechains in the precursors determines the level of fluorination present in the side chain, $R_1$ of the final compound IV. According to the methods of the present invention, a compound of formula V having no fluorine substitutions in the allylic side chain will yield final compounds IV having a structure designated by EF1,1. The 1,1 represents 1 fluorine atom on carbon 2 and 1 fluorine atom on carbon 3, as fluorine adds to the adjacent carbons of the double bond. Allyl precursors having 1 fluorine substitution in the side chain will yield final compounds having EF1,2 or EF2,1 structures, depending on whether the allyl sidechain was substituted on the second or terminal carbon atom of the sidechain. Allyl precursors having 2 degrees of fluorine substitution will yield final products EF2,2 and EF1,3; and those having 3 degrees of fluorination will yield EF5.

Another aspect of the present invention, provides methods for detecting tissue hypoxia. Imaging methods comprise using the novel compounds of the invention with or without immunohistochemical assays, preferably without the use of monoclonal antibodies to detect hypoxic cells.

For example, in a non-invasive assay, according to the invention, a mammal is administered a compound of the invention comprising an effective amount of the compound dissolved or dispersed in a suitable pharmaceutical carrier or diluent such as non-pyrogenic physiological saline. An effective amount of the compound can be easily determined by those skilled in the art. Any such diluents known to those skilled in the art may be used without departing from the spirit of the invention. The compound is allowed to partially clear from the mammal and to be taken up preferentially through the bioreductive metabolism of hypoxic cells, and then a portion of the mammal containing the tissue of interest is analyzed non-invasively, such as through positron emission tomography (PET). A proportion of the compound will remain in the body, bound or associated with hypoxic cells. Tissue hypoxia is assayed using detectors of the marker atoms. In the case of PET, a compound of the invention must first be formulated with the positron emitting isotope $^{18}$F. Because of the half-life of radioactive fluorine (110 min) a compromise must be reached between having the maximum clearance (providing the best signal: noise ratio) and having enough signal to provide adequate image resolution.

Imaging techniques suitable for practicing the invention include, but are not limited to, PET and SPECT (single photon emission computed tomography). Generally, imaging techniques involve administering a compound with marker atoms that can be detected externally to the mammal.

A particularly preferred imaging method for practicing the claimed invention is PET. When the detection technique is PET, the preferred compound has the formula IV:

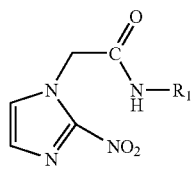

IV wherein $R_1$ is selected from the group consisting of —$CH_2$—CHF—$CH_2$F, —$CH_2$—CHF—$CHF_2$, —$CH_2$—CHF—$CF_3$, —$CH_2$—$CF_2$—$CHF_2$, and —$CH_2$—$CF_2$—$CF_3$; and provided that at least one F is $^{18}$F, which is a positron imaging isotope.

For purposes of the current invention, mammals include, but are not limited to the Order Rodentia, such as mice and rats; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The preferred mammals are humans.

The invention is further directed to pharmaceutical formulations of the novel drug compounds. In accordance with preferred embodiments, a compound of the invention is dissolved or dispersed in a pharmaceutically acceptable diluent. Preferred diluents are non-pyrogenic physiological saline.

Generally, the compounds of the invention can be synthesized using various reaction conditions depending on the starting material and ultimate requirements. Precursors are provided and fluorinated with $F_2$ or [$^{18}$F]-$F_2$. Making of PET isotope-containing derivatives requires rapid addition of the $^{18}$F moiety followed by immediate purification and use because of the half-life of $^{18}$F, 110 minutes.

In preferred embodiments of the present invention, the preparation of unlabeled PET compounds generally requires that the precursors be dissolved in a suitable organic solvent at a temperature ranging from −15° to 100° C., depending on the solvent employed. Preferred solvents include organic acids including, but not limited to, carboxylic acids such as HCOOH, $CH_3COOH$, $CFH_2COOH$, $CF_2HCOOH$, $CF_3COOH$. Preferably, the precursors are dissolved in $CF_3COOH$ at a temperature ranging from −5° C. to 5° C., with 0° C. being most preferred. $F_2$ gas is then bubbled through the solution to effect an electrophilic fluorination across the double bond. The solvent is evaporated and the residue is dissolved in a suitable solvent, such as methanol: water (1:1). The mixture is filtered and the organic solvent evaporated to obtain the residue. After the organic acid is evaporated, the residue is purified, preferably by HPLC.

In other preferred embodiments, the preparation of [$^{18}$F]-labeled compounds generally requires a procedure similar to that described above. The precursor is dissolved in a suitable organic solvent, such as an organic acid. Preferred solvents include carboxylic acids, for example, HCOOH, $CH_3COOH$, $CFH_2COOH$, $CF_2HCOOH$, $CF_3COOH$ with $CF_3COOH$ being most preferred. The reaction may take place at a temperature ranging from −15° to 100° C., depending upon the solvent employed. −5° C. to 5° C., is a preferred range when $CF_3COOH$ is used with 0° C. being most preferred. [$^{18}$F]-$F_2$ gas is then bubbled through the solution to effect an electrophilic fluorination across the double bond. The resulting solution is evaporated to dryness under reduced pressure, such as from 0 to 1 atm.

In the case of 2-nitroimidazole compounds, while not bound to any particular theory, it is believed that employing a strong organic acid to dissolve the precursor, such as trifluoroacetic acid, in the fluorination reaction produces superior results for at least three reasons. First, the organic acid acts to protonate the nitrogen atom in position 3 of the imidazole ring, thereby decreasing electron density in the ring. This decreased electron density protects the nitroimidazole ring and its nitro group from electrophilic attack by fluorine, making the allyl double bond a main target. Also, the acid facilitates removal of the impurity F by converting it to HF, which is easily removed from the solution during evaporation. Third, the precursor's solubility is enhanced in a strong organic acid which results in a more efficient product yield.

It should be noted that the amount of fluorine gas should be controlled carefully, and the reaction should be stopped once the starting material is consumed to prevent the imidazole ring or amido group from further reaction with fluorine.

In some embodiments of the present invention, the novel compounds of the of the invention are generally [$^{18}$]-fluorine derivatives of propylamine. It is contemplated that these novel compounds may be introduced into compositions and compounds, comprising, among others, antibodies, receptors, protein conjugates, and other biologically active compounds. To make such compounds or compositions PET agents, $^{18}$F is introduced by electrophilic fluorination of fluorinated alkenes. Generally, such a method would include conjugating a propylamine-based side chain with a carboxyl group of the compound or composition of interest ($R_5$COOH), forming $R_5$CONH$R_6$, where $R_6$ may be —$CH_2$—CX=CYZ, wherein at least one of X, Y, and Z is fluorine. The next step is the introduction of $^{18}$F as described above. Any such compounds or compositions containing the novel sidechains of the invention are contemplated to be within the scope of the invention, as are the methods for making the same.

The reaction may yield a reaction slurry from which the product must be recovered. Methods of recovering the sample include any filtration or separation techniques known in the art. Such methods include, but are not limited to, vacuum filtration, separatory extraction, or distillation. A preferred method is filtration using air or liquid, but other methods will be apparent to those skilled in the art.

The filtration solid may further require washing with organic solvents to separate out impurities or other reaction intermediates or byproducts. Organic solvents include, but are not limited to, ether, methanol ethanol ethyl acetate, or hexanes. Ethyl acetate is a preferred solvent, but other types of solvents will be apparent to those skilled in the art. Any organic solvent should be evaporated using methods known in the art. Evaporation methods may be accomplished at room temperature, by vacuum, aspiration, or by using latent heat. The evaporation methods are not limited to these techniques and other techniques will be apparent to those skilled in the art.

The reaction product is then purified using purification techniques known in the art. These techniques include, but are not limited to, column chromatography, flash chromatography, recrystallization, or gel chromatography. When using chromatographic purification methods, gradient elution is preferred. Combinations of organic solvents include, but are not limited to, methanol acetonitrile, hexanes, carbon tetrachloride, and ethyl acetate. Other purification methods will be apparent to those skilled in the art.

Preferred aspects of the invention are discussed in the following examples. While the present invention has been described with specificity in accordance with certain of its preferred embodiments, the invention is not so limited.

EXAMPLES

Reagents and solvents were purchased from Aldrich Chemical Co. and used without additional purification unless otherwise noted. $^1$H NMR spectra were recorded on a Bruker-AMX-300 using $CDCl_3$ or acetone-$d_6$ as solvent and tetramethylsilane as an internal standard; $^{19}$F NMR spectra were measured on a Varian XL at 282 MHz, referenced to external $CF_3COOH$ in $D_2O$. HPLC was performed on a Waters system (with Waters UV detector and radioactivity detector from IN/US Service Corp., Fairfield, N.J.) using an Altima C-18 column (5 µm particle size, 4 mm×250 mm) and ammonia-acetate buffer containing 40% $CH_3OH$ (pH=4.7, final concentration 0.1 M) as a mobile phase (flow rate 1 ml/min) with serial detection of 325 nm absorbency (specific for 2-nitroimidazole moiety) and radioactivity. The same HPLC conditions were used for the purification of [$^{18}$F]-EF5.

Example 1

Synthesis of 2,3,3-trifluoro allyl amine hydrochloride 2,3,3-trifluoro allyl amine hydrochloride was prepared following the general procedure described in *Castelhano*, et al, "Synthesis of α-amino acids with β, γ-unsaturated side chains," *Tetrahedron*, 1988 44 (17), 5451–5466, herein incorporated by reference in its entirety, through the following intermediate compounds:

A. 3,4,4-trifluoro-2-benzyloxycarbonylamino-but-3-enoic acid methyl ester, which was generally prepared from N-(benzloxycarbonyl)-a-chloroglycinate by converting the N-(benzyloxycarbonyl)-a-chloroglycinate into the methyl ester as described by Castelhano et al., "Reactions of an electrophilic glycine cation equivalent with Grignard reagents. A simple synthesis of β, γ-unsaturated amino acids, *Tetrahedron Letters,*1986 27 (22), 2435–8, herein incorporated by reference in its entirety.

$^1$H (300 MHz, $CDCl_3$) 3.82 (s, 3H), 5.13 (s, 2H), 5.06–5.17 (brd, 1H), 5.26,5.68 (brd, 1H), 7.34 (s, 5H). $^{19}$F (282 MHz, $CDCl_3$)–101.47 (dd, J=34 Hz, J=71.0 Hz, 1F), –119.66(dd,J=71.0 Hz,J=115 Hz, 1F),–187.28(ddd,J=115 Hz,J=34 Hz,J=28 Hz, 1F).

B. N-(benzyloxycarbonyl)-(alpha)-chloroglycinate was generally synthesized according the procedures described by Williams, et al. "General synthesis of β-γ, alkynylglycine derivatives," *Journal of Organic Chemistry*, 1990 55(15), 465757–63, herein incorporated by reference in its entirety.

$^1$H (300 MHz, $CDCl_3$) 3.85 (s, 3H), 5.20 (s,2H), 6.15 (s, 2H), 7.35 (s, 5H).

Final compound, 2,3,3-trifluoro allyl amine hydrochloride gave a white solid (3.87 g, 66%).

$^1$H (300 MHz, $CDCl_3$) 3.84 (dm, J=21.3 Hz, 1H). $^{19}$F (282 MHz, D2O)–96.94 (dd, J=32 Hz, J=68 Hz, 1F), –115.15 (dd, J=68 Hz, J=115 Hz, 1F), –178.9 (ddt, J=21 Hz, J=32.1 Hz, J=115 Hz,1F).

Example 2

Synthesis of 2-(2-nitro-1H-imidazol-1-yl)-N-(2,3,3-trifluoroallyl)-acetamide

N-methylmorpholine (1.01 g, 10 mmol) was added to 2-(2-nitro-1H-imidazol-1-yl)acetic acid (1.71 g, 10 mmol) in 150 mL of dry THF under nitrogen at 0° C. and stirred for 10 minutes. Isobutyl chloroformate (1.43 mL, 11 mmol) was added. After 30 minutes, 1,1,2-Trifluoro allyl amine hydrochloride (1.62 g, 11 mmol) and N-methylmorpholine (1,21 g, 12 mmol) was added to the solution and the mixture stirred at room temperature overnight. The solution was then filtered and the organic solvent evaporated to give a pale yellow solid.

$^1$H (300 MHz, $CD_3COCD_3$) 4.24 (dm, J=21.3 Hz, 1H), 5.34 (s, 2H), 7.19 (s,1H), 7.56 (s, 1H), 8.10 (br, 1H). $^{19}$F. (282 MHz, $CD_3COCD_3$) –102.2 (dd, J=32 Hz, J=81 Hz, 1F), –118.6 (dd,J=81 Hz, J=113 Hz, 1F), –176.0 (ddt, J=21.4 Hz, J=32 Hz, J=113 Hz, 1F);

Anal.Calcd for $C_8H_3F_3N_4O_3$: C, 36.36; H, 2.65; N, 21.21. Found:C, 36.84; H, 2.60; N, 20.71.

Example 3

Preparation of 2-(2-Nitro-1H-imidazol-1-yl)-N-ayly-acetamide 2-(2-nitro-1H-imidazol-1-yl)-acetic acid (1.71 g, 10 mmol) was added to N-methylmorpholine (1.01 g, 10 mmol) in 150 ml of dry THF under nitrogen at 0° C. and stirred for 10 minutes until completely dissolved. Isobutyl chloroformate (1.43 ml, 11 mmol) added. After 30 minutes, allylamine hydrochloride (1.03 g, 11 mmol) and N-methylmorpholine (1.21 g, 12 mmol) added to the solution and the mixture stirred at room temperature overnight. The solution was then filtered and the organic solvent was evaporated to give a pale yellow solid. Purification by chromatography (silica gel, $CH_3OH/CHCl_3$=10:1) gave a white solid (1 g, 48%).

Example 4

Synthesis of 2-fluoroallylamine hydrochloride

A. Themixture 2-fluoro-3-chloro-1-propyl bromide and 1-fluoro-3-chloro-2-propyl bromide was generally prepared as described by Olah, et al., *Synthesis,* 1973, 4, p. 780, herein incorporated by reference in its entirety.

B. Potassium t-butoxide (2.24 g, 20 mmol) in 20 mL of THF was added dropwise to the mixture of 2-fluoro-3-chloro-1- propyl bromide and 1-fluoro-3-chloro-2-propyl bromide (1.76 g, 10 mmol) at −70° C. and stirred for 0.5 hour, then the solution and kept at −20° C. for 1.5 hour. After the mixture was cooled down to −60° C., acetic acid was added to quench the reaction. The solution obtained by vacuum transfer was then mixed with sodium azide (1.3 g, 20 mmol) in DMSO (20 mL) and stirred overnight. By further vacuum transfer, the obtained mixture was added dropwise to $PPh_3$ (2.62 g, 10 mmol) in 10 mL of THF and 0.36 mL of $H_2O$ and stirred at room temperature overnight. The solution was subjected to another vacuum transfer to provide 2-fluoro-allyl amine in a mixture of solvents, into which HCl gas was bubbled. 2-Fluoro-allyl amine hydrochloride was obtained by filtration (25%).

$^1$H NMR (300 MHz, $H_2O$) (3.63 (d, J=16 Hz, 2H), 4.66 (dd, J=4 Hz, J=49 Hz, 1H) 4.81 (dd, J=4 Hz, J=16 Hz, 1H).

$^{19}$F NMR (282 MHz, $H_2O$) (−106.3 (dq, J=16 Hz, J=49 Hz, 1F).

Example 5

Synthesis of 2-(2-nitro-1H-imidazol-1-yl)-N-(2-fluoro-allyl)acetamide

N-methylmorpholine (1.01 g, 10 mmol) was added to 2-(2-nitro-1H-imidazol-1-yl)-acetic acid (1.71 g, 10 mmol) in 150 mL of dry THF under nitrogen at 0° C. and stirred for 10 minutes. Isobutyl chloroformate (1.43 mL, 11 mmol) was added. After 30 minutes, 2-fluoro allyl amine hydrochloride (1.23 g, 11 mmol) and N-methylmorpholine (1.21 g, 12 mmol) was added to the solution and the mixture was stirred at room temperature overnight. The solution was filtered and the organic solvent evaporated to give a yellow solid. Purified by column afforded a light yellow solid (1.1 g, 50%).

$^1$H NMR (300 MHz, $CDCl_3$) (4.05 (dd, J=6 Hz, J=14 Hz, 2H), 4.55 (dd, J=4 Hz, J=49 Hz, 1H) 4.76 (dd, J=4 Hz, J=16 Hz,1H), 5.07 (s, 2H), 6.12 (br,1H), 7.18 (s,1H), 7.24 (s,1H).

$^{19}$F NMR (282 MHz, $CDCl_3$) (−104.6 (dq, J=14 Hz, J=49 Hz, 1F).

Anal.Calcd for $C_8H_9FN_4O_3$ C, 42.10; H, 3.95, N, 24.56. Found C, 42.06; H: 3.98, N, 24.15.

Example 6

Synthesis of 1,1-Difluoroallyl amine hydrochloride 1,1-Difluoro-1-bromo-propylamine hydrochloride (0.21 g, 1 mmol) was mixed with potassium t-butoxide (0.3 g, 3 mmol) in 5 mL of THF and stirred for 3 hours at room temperature. The solution obtained by vacuum transfer was then subjected to anhydrous HCl. 3,3-Difluoroallyl amine hydrochloride was provided by filtration (90%).

$^1$H NMR (300 MHZ, $H_2O$) (3.51 (dt, J=8 Hz, J=2 Hz, 2H), 4.54 (ddt, J=2 Hz, J=8 Hz, J=24 Hz,1H). $^{19}$F NMR (282 MHz, $H_2O$) (−87.7(d, J=49 Hz, 1F), −89.4 (dd, J=49 Hz, J=26 Hz, 1F).

Example 7

Synthesis of 2-(2-Nitro-1H-imidazol-1-yl)-N-(3,3-difluoro-allyl)acetamide

The compound was synthesized similarly as for 2-(2-nitro-1H-imidazol-1-yl)-N-(2-fluoro-allyl)acetamide. Yield: 58%.

$^1$H NMR (300 MHz, $CD_3COCD_3$) (3.86 (m, 2H), 4.53 (ddt, J=3 Hz, J=16 Hz, J=25 Hz, 1H), 5.22 (s, 2H), 7.13(s, 1H), 7.49 (s,1H), 7.75 (br,1H).

$^{19}$F NMR (282 MHz, $CDCl_3$) (−89.6 (d, J=45 Hz, 1F), −91.0(dd, J=25 Hz, J=45 Hz, 1F).

Anal.Calcd for $C_8H_9F_2N_4O_3$ C, 39.02; H, 3.25, N, 22.76. Found C, 39.13; H, 3.30, N: 22.52

Example 8

Synthesis of EF5 from allyl precursor by addition of $F_2$ 2-(2-Nitro-1H-imidazol-1-yl)-N-(2,3,3-trifluoro-allyl)-acetamide (50 mg, 0.20 mmol) was dissolved in 4 mL of trifluoroacetic acid at room temperature. 10% $F_2$ was bubbled into the solution for 30 minutes (flow rate=10 mL/min). The solvent was evaporated and the residue was triturated in the presence of ethyl acetate. A white solid was filtered and the organic solvent evaporated to get the residue, which was purified by chromatography (silica gel, $CH_3OH$/$CHCl_3$=8:1) to give2-(2-Nitro-1H-imidazol-1-yl)-N-(2,2,3,3,3-pentafluoropropyl)-acetamide (18 mg, 32%). Decrease of fluorine concentration in gas mixture causes more efficient consumption, simultaneously decreasing the overall EF5 yield. Reaction of 25 mg of precursor (0.11 mmol) in 5 mL of trifluoroaceticacid with an equivalent amount of 0.1% $F_2$ (flow rate 100 mL/min during 25 min) causes a complete consumption of allyl precursor, yielding 11% EF5.

$^1$H (300 MHz, $CD_3COCD_3$) 4.06 (dt, 2H), 5.37 (s, 2H), 7.15 (s, 1H), 7.54 (s,1H), 8.22 (br, 1H).

$^{19}$F NMR (282 MHz, $CD_3COCD_3$) −81.70 (s, 3F),−118.76 (t, J=16 Hz, 2F).

Example 9

Synthesis of $^{18}$F-labeled EF5 from allyl precursor

[$^{18}$F]-2-(2-Nitro-1H-imidazol-1-yl)-N-(2,2,3,3,3-pentafluoropropyl)-acetamide.

[$^{18}$F]-$F_2$ was prepared by the $^{20}$Ne(d,)$^{18}$F reaction using 50 mL target filled with 1% $F_2$/Ne and pressurized with Ne to 10 atm. The [$^{18}$F]-$F_2$ (0.1% in Ne, 20 mCi specific activity 0.2 Ci/mmol) was bubbled through 4 mL of trifluoro acetic acid (TFA) containing 2-(2-Nitro-1H-imidazol-1-yl)-N-(2,3,3-trifluoro-allyl)-acetamide (15 mg, 0.06 mmol) in a 15 mL polypropylene tube at 0° C. for 20 minutes. The resulting mixture was transferred into a 50 mL flask of a rotary evaporator with a $K_2CO_3$ trap placed between the condenser and the pump. The solution was evaporated to dryness under reduced pressure at 50° C. This removes the solvent TFA and the major impurity [$^{18}$F]-F in the form of HF, which is further trapped by $K_2CO_3$. FIG. 1 represents an HPLC analysis of the reaction mixture of the products of [$^{18}$F]-EF5 synthesis after the evaporation of the solvent with simultaneous detection of radioactivity (solid line) and UV absorbency (dotted line). Peak at 6 min represents the precursor; EF5 is eluted at 11–12 min.

The residue was dissolved in 0.5 mL of 0.1 M ammonia-acetate buffer (pH=4.7) containing 40% $CH_3OH$, centrifugated 1 min at 1400 g and the supernatant was injected into preparative HPLC column. Purification conditions: Alltech Econosil C-18 colum (10 μm particle size, 10×250 mm), 0.1 M ammonia-acetate buffer (pH=4.7) containing 37% CH3OH as a mobile phase (flow rate 2 mL/min, pressure 1500 psi); detection of the solution absorption at 325 nm. The fraction containing EF5 (retention time may vary between the columns from 30 to 40 min; the exact retention time has to be determined by the injection of EF5 prior to the experiment) was collected and evaporated to dryness at reduced pressure at 90° C. during 15 minutes. This treatment removes the following components of buffer: CH₃OH, H₂O, acetic acid, ammonium acetate. Typical time of the preparation is 1.5–2 hrs. The residue contains about 2 mg of [18F]-EF5 with 1 mCi of activity, corrected radiochemical yield 10–12%.

Example 10

PET Analysis of a Tumor-bearing Rat Treated with [$^{18}$F]-EF5

Figure 3:
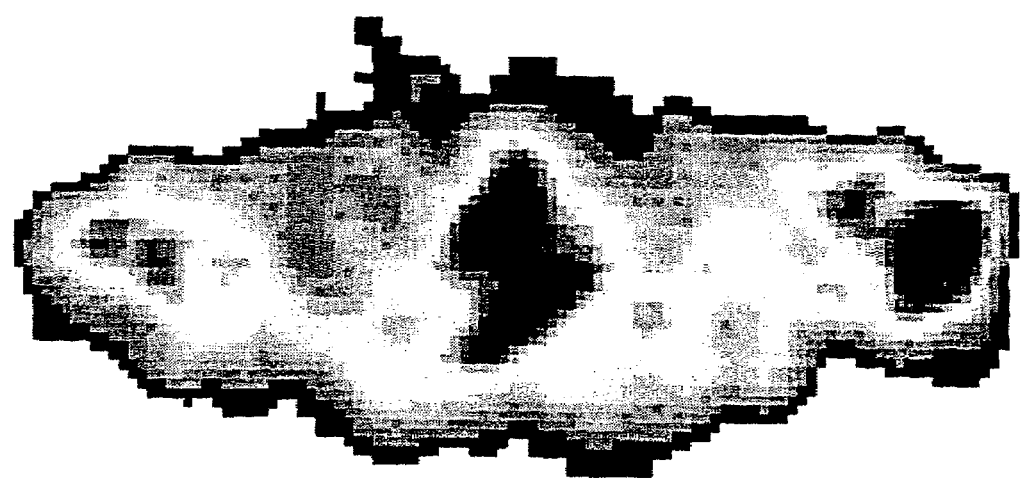
FIG. 3 shows a transverse PET image of a rat bearing hypoxic Q7 tumor in the right leg. The dark spot on the right side of the image represents a tumor and the dark spot in the middle of the image represents a bladder.

FIG. 3 illustrates a PET image of a tumor-bearing rat treated with 18-F-labeled EF5, 150 minutes post injection. The dark spot in the right side of the image represents the tumor and the dark spot in the middle of the inage represents the bladder.

Q7 cells were obtained from the American Type Culture Collection (ATCC). They were maintained in exponential growth by transfers at 3.5 day intervals with standard culture conditions. Growth medium was Eagle's MEM supplemented with 15% fetal calf serum and standard penicillin and streptomycin.

All animal studies conformed to the regulations of the University of Pennsylvania Institutional Animal Care and Use Committee. Male Buffalo rats (Harlan Sprague Dawley, Indianapolis, Ind., USA) were used for all studies. Donor tumors were created by injecting 1 million Q7 cells subcutaneously into the thigh region. The average growth time to achieve a 1 cm diameter tumor was 21 days. Tumors of less than 2 g were used in the experiments.

The tumor (Morris 7777 hepatoma)is clearly visible even though various organs also expected to bind the drug were nearby (bladder, digestive tract).

Example 11

Analysis of the Distribution of Radioactive Drug in Various Organs and Tissues

To measure the distribution of radioactive drug in various organs and tissues, the solution of [$^{18}$F]-EF5 in saline buffer was injected I/V into 3 male Buffalo rats. Animals were sacrificed after 3 hours and the samples of tissues were collected and weighted. The radioactivity of samples was measured by γ-counter and corrected for weight and the time of decay.

Table 1 shows the actual distribution of radioactive counts from various organs and tissues after animal sacrifice and tissue collection. Results from 3 animals are shown.

TABLE 1

Tissue distribution of [$^{18}$F]-EF5 in rats bearing tumors (% dose/gram)

| Organ | 3 hrs | 3 hrs | 4 hrs |
|---|---|---|---|
| Blood | 0.260 | 0.279 | 0.238 |
| Brain | 0.116 | 0.176 | 0.150 |
| Liver | 0.399 | 0.578 | 0.489 |
| Spleen | 0.192 | 0.294 | 0.242 |
| Kidney | 0.510 | 0.650 | 0.500 |
| Muscle | 0.162 | 0.246 | 0.187 |

TABLE 1-continued

Tissue distribution of [$^{18}$F]-EF5 in rats bearing tumors (% dose/gram)

| Organ | 3 hrs | 3 hrs | 4 hrs |
|---|---|---|---|
| Bone | 0.040 | 0.079 | 0.071 |
| Lung | 0.217 | 0.357 | 0.326 |
| Heart | 0.209 | 0.318 | 0.277 |
| Intestine | 0.410 | 0.477 | 0.376 |

Those skilled in the art will appreciate that numerous changes and modifications may be made to the preferred embodiments of the present invention, and that such changes and modifications may be made without departing from the spirit of the invention. It is, therefore, intended that the spirit and scope of the appended claims should not be limited to the description of the preferred embodiments contained herein, but, that the appended claims cover all such equivalent variations as fall within the true spirit and scope of the invention.

What is claimed is:

1. A method comprising the step of contacting a compound having formula:

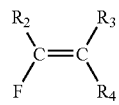

wherein:
   R$_2$, R$_3$, and R$_4$ are independently selected from the group consisting of H, halogen, alkyl, heteroalkyl, cycloalkyl, hetero cycloalkyl, aryl, heteroaryl, alkoxy, aminoalkyl, hydroxyalkyl, ether, amide, keto, and carboxyl;
   with F$_2$ in the presence of an organic acid solvent for a time and under conditions effective to form a compound having the formula:

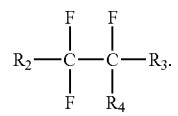

2. The method of claim 1 wherein at least one of R$_2$, R$_3$, and R$_4$ is an aryl, wherein said aryl being substituted with at least one nitrogroup.

3. The method of claim 2 wherein R$_2$ is an aryl, wherein said aryl being substituted with at least one nitrogroup and R$_3$ and R$_4$ are independently hydrogen or fluorine.

4. The method of claim 3 wherein R$_3$ and R$_4$ are F.

5. The method of claim 1 wherein said organic acid solvent is selected from the group consisting of HCOOH, CH$_3$COOH, CFH$_2$COOH, CHF$_2$COOH, CF$_3$COOH.

6. The method of claim 3 wherein said organic acid solvent is CF$_3$COOH.

7. The method of claim 3 wherein said aryl being substituted with at least one nitrogroup has the formula:

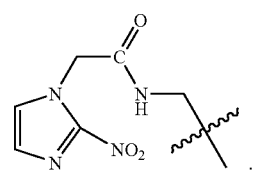

8. A method comprising the step of:
contacting a precursor having the formula:

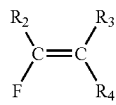

$R_2$, $R_3$, and $R_4$ are independently selected from the group consisting of H, halogen, alkyl, heteroalkyl, cycloalkyl, heterocycloalkyl, aryl, heteroaryl, alkoxy, aminoalkyl, hydroxyalkyl, ether, amide, keto, and carboxyl;

with $-F_2$ in the presence of an organic acid solvent for a time and under conditions effective to form a compound having the formula:

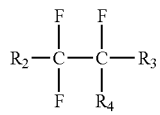

wherein at least one F is $^{18}F$.

9. The method of claim 8 wherein at least one of $R_2$, $R_3$, and $R_4$ is an aryl, wherein said aryl is substituted with at least one nitrogroup.

10. The method of claim 9 wherein $R_3$ and $R_4$ are, independently, hydrogen, F, or $^{18}F$.

11. The method of claim 10 wherein $R_3$ and $R_4$ are independently F or $^{18}F$.

12. The method of claim 9 wherein wherein said aryl being substituted with at least one nitrogroup has the formula:

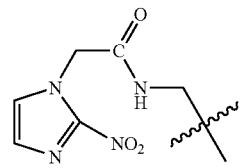

13. The method of claim 8 wherein said organic acid solvent is selected from the group consisting of HCOOH, $CH_3COOH$, $CFH_2COOH$, $CHF_3COOH$, and $CF_3COOH$.

14. The method of claim 10 wherein said organic acid solvent is $CF_3COOH$.

* * * * *

UNITED STATES PATENT AND TRADEMARK OFFICE
CERTIFICATE OF CORRECTION

PATENT NO.         : 7,230,115 B1
APPLICATION NO.    : 10/297454
DATED              : June 12, 2007
INVENTOR(S)        : William R. Dolbier et al.

It is certified that error appears in the above-identified patent and that said Letters Patent is hereby corrected as shown below:

Title Page,
Item (22) PCT Filed:
Delete "Apr. 20, 2000" and insert -- Jul. 20, 2000 --.

Column 4,
Line 5, delete "One.," and insert -- Onc., --.
Line 36, delete "2(2-nitroimidazol-1[H]" and insert
-- 2-(2-nitroimidazol-1[H] --.

Column 5,
Line 10, after "alkyl" insert -- , --.
Line 10, after "cycloalkyl" insert -- , --.

Column 6,
Line 2, delete "EF 1,1" and insert -- EF1,1--.

Column 7,
Line 34, after "alkyl" insert -- , --.
Line 34, after "heteroalkyl" insert -- , --.
Line 34, after "cycloalkyl" insert -- , --.
Line 35, after "aryl" insert -- , --.
Line 35, after "heteroaryl" insert -- , --.
Line 35, after "aminoalkyl" insert -- , --.
Line 36, after "hydroxyalkyl" insert -- , --.

Column 9,
Line 36, delete "Camivora," and insert -- Carnivora, --.
Line 52, delete "[$^{18}$]F-F$_2$." and insert -- [$^{18}$F]-F$_2$.--.

Column 10,
Line 29, delete "F" and insert -- F$^-$ --.
Line 40, delete "of the" (second occurrence).
Line 40, delete "[$^{18}$]-flourine" and insert -- [$^{18}$F]-flourine --.

UNITED STATES PATENT AND TRADEMARK OFFICE
CERTIFICATE OF CORRECTION

PATENT NO. : 7,230,115 B1
APPLICATION NO. : 10/297454
DATED : June 12, 2007
INVENTOR(S) : William R. Dolbier et al.

It is certified that error appears in the above-identified patent and that said Letters Patent is hereby corrected as shown below:

Column 11,
Line 56, delete "N-benzloxycarbonyl)" and insert -- N-(benzyloxycarbonyl) --.

Column 12,
Line 36, delete "$C_8H_3F_3N_4O_3$:" and insert -- $C_8H_7F_3N_4O_3$: --.
Line 41, delete "N-ayly-" and insert -- N-allyl- --.
Line 61, delete "Themixture" and insert -- The mixture --.

Column 13,
Line 2, delete "-70° C." and insert -- ⁻70° C. --.

Column 14,
Line 6, delete "$C_8H_9F_2N_4O_3$ C," and insert -- $C_8H_8F_2N_4O_3$ C, --,
Line 12, after "$F_2$" insert -- , --.
Line 27, delete "(0.11 mmol)" and insert -- (0.1 mmol) --.
Line 54, delete "[$^{18}$F]-F" and insert -- [$^{18}$F]-F⁻ --.
Line 65, delete "colum" and insert -- column --.

Column 15,
Line 21, delete "inage" and insert -- image --.

Column 16,
Line 34, delete "hetero cycloalkyl," and insert -- heterocycloalkyl, --.
Line 46, delete "aryl," and insert -- aryl or heteroaryl, --.
Line 46, delete "being" and insert -- is --.
Line 48, delete "aryl," and insert -- aryl or heteroaryl, --.
Line 49, delete "being" and insert -- is --.
Line 51, delete "F." and insert -- fluorine. --.
Line 57, delete "aryl being" and insert -- aryl or heteroaryl --.

Column 17,
Line 15, delete "-$F_2$" and insert -- [$^{18}$F]-$F_2$ --.

UNITED STATES PATENT AND TRADEMARK OFFICE
CERTIFICATE OF CORRECTION

PATENT NO. : 7,230,115 B1
APPLICATION NO. : 10/297454
DATED : June 12, 2007
INVENTOR(S) : William R. Dolbier et al.

It is certified that error appears in the above-identified patent and that said Letters Patent is hereby corrected as shown below:

<u>Column 18,</u>
Line 2, delete "aryl, wherein said aryl is" and insert -- aryl or heteroaryl, wherein said aryl or heteroaryl is --.
Lines 8-9, delete "aryl being" and insert -- aryl or heteroaryl --.

Signed and Sealed this

Twenty-fourth Day of June, 2008

JON W. DUDAS
*Director of the United States Patent and Trademark Office*